United States Patent [19]

Carlsson et al.

[11] 4,336,267
[45] Jun. 22, 1982

[54] HEART ACTIVE COMPOUNDS AND METHODS OF USE

[75] Inventors: Enar I. Carlsson, Kungsbacka; Nils H. A. Persson, Dalby; Gustav B. R. Samuelsson, Molnlycke; Kjell I. L. Wetterlin, Sandby, all of Sweden

[73] Assignee: Aktiebolaget Hässle, Goteborg, Sweden

[21] Appl. No.: 150,883

[22] Filed: May 19, 1980

Related U.S. Application Data

[62] Division of Ser. No. 549,841, Feb. 13, 1975, Pat. No. 4,244,969.

[30] Foreign Application Priority Data

Feb. 14, 1974 [SE] Sweden .............................. 7401958

[51] Int. Cl.³ .................... A61K 31/24; C07C 101/72
[52] U.S. Cl. .................... 424/309; 260/456 A; 424/303; 424/324; 424/330; 560/39; 562/444; 564/165; 564/344; 564/349; 564/350; 564/351
[58] Field of Search .................. 560/39; 564/165, 344, 564/349, 350, 351; 562/444; 424/309, 324, 330, 303; 260/456 A

[56] References Cited

U.S. PATENT DOCUMENTS 3,793,365  2/1974  Winter et al. ........................ 562/444

*Primary Examiner*—Sam Rosen

*Attorney, Agent, or Firm*—Brumbaugh, Graves, Donohue & Raymond

[57] ABSTRACT

This invention relates to novel compounds of the general formula

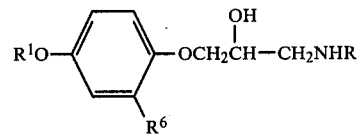

Representative compounds within the scope of the invention are

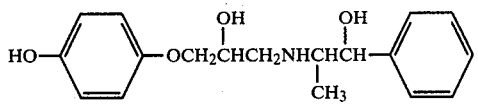

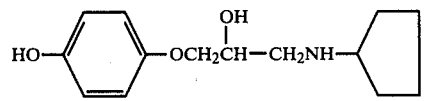

The compounds are disclosed as being useful for treating symptoms and signs of cardiac failure by stimulating the β-receptors of the heart. Methods of treatment using these compounds are discussed.

12 Claims, No Drawings

HEART ACTIVE COMPOUNDS AND METHODS OF USE

This is a division of application Ser. No. 549,841 filed Feb. 13, 1975, now U.S. Pat. No. 4,244,969.

Many heart diseases create such extensive damage to the muscle of the myocardium that a heart insufficiency occurs. A fundamental component in the therapy of heart insufficiency is an agent which has a positive inotropic action on the heart (i.e., one which increases the contractile force of the heart) and/or which has a positive chronotropic action on the heart (i.e., one which increases the heart beat frequency).

Presently, the most commonly used agents are the glycosides of digitalis which have inotropic action. However, the digitalis preparations show evident drawbacks from a therapeutic point of view. They have a low therapeutic range. For example, they cause arrythmogenetic effects in the heart, even when the dosage insignificantly exceeds the dosage which has a positive inotropic effect. Thus, there is an evident therapeutic need of positive acting agents which can replace or complement the digitalis preparations.

The present invention relates to new potent β-receptor stimulating compounds as well as their preparation and a method for treating symptoms and signs of cardiac failure by stimulating the β-receptors of the heart by administering to mammals, including man, these new compounds.

The new compounds are those of the general formula

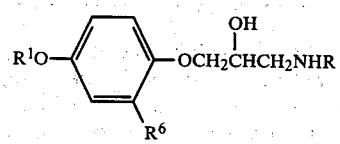

wherein
(a) $R^1$ is selected from the group consisting of hydrogen, benzyl, tosyl, mesyl and

$R^5$ being hydrogen, straight or branched aliphatic alkyl having 1 to 7 carbon atoms, phenyl, benzyl, and phenylethyl, wherein the phenyl nucleus may be further substituted with alkyl having 1 to 4 carbon atoms, alkoxy having 1 to 4 carbon atoms, alkoxyalkyl having 2 to 8 carbon atoms or halogen, in any position;

(b) R is selected from the group consisting of cycloalkyl having at most 6 carbon atoms and

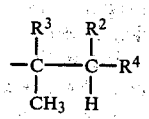

wherein $R^2$ is selected from the group consisting of hydrogen and hydroxy, $R^3$ is selected from the group consisting of hydrogen and methyl, $R^4$ is selected from the group consisting of

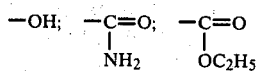

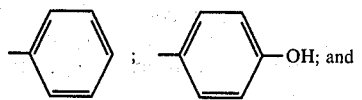

when $R^2$ is hydrogen, and $R^4$ is selected from the group consisting of

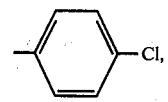

when $R^2$ is hydroxy; and
(c) $R^6$ is selected from the group consisting of hydrogen, halogen and allyl.

Within this class of compounds there are certain preferred structures which should be noted:

1. When R is cycloalkyl it preferably has 5 to 6 carbon atoms, such as cyclopentyl and cyclohexyl.
2. An aliphatic alkyl $R^5$ is preferably selected from the group consisting of methyl, ethyl, propyl, isopropyl, butyl, isobutyl, sec. butyl, tert.-butyl, amyl, isoamyl, 2,2-dimethylpropyl, tert.-amyl, hexyl, iso-hexyl, 1,1-dimethylbutyl.
3. When $R^5$ is a phenyl group substituted with halogen, the substituent halogen may be in any position.
4. When $R^5$ is a phenyl group substituted with an alkoxyalkyl group, representative substituents are methoxymethyl, ethoxymethyl, ethoxyethyl, methoxyethyl, methoxypropyl and methoxybutyl.

Typical compounds according to the present invention are:

1-[2-phenyl-2-hydroxy-1-methylethylamino]-3-p-hydroxyphenoxy-propanol-2;
Ethyl-3-[3-p-hydroxyphenoxy-2-hydroxy-propylamino]-butyrate;
3-[3-p-hydroxyphenoxy-2-hydroxypropylamino]-butyramide;
1-[hydroxytert.butylamino]-3-p-hydroxyphenoxy-propanol-2;
1-[2-(p-hydroxyphenyl)-1-methylethylamino]-3-p-hydroxyphenoxy-propanol-2;
1-[2-(p-hydroxyphenyl)-1,1-dimethylethylamino]-3-p-hydroxyphenoxy propanol-2;
1-[2-(p-chlorophenyl)-1-methylethylamino]-3-p-hydroxyphenoxy propanol-2;
1-cyclopentylamino-3-p-hydroxyphenoxy propanol-2;
1-[2-(p-hydroxyphenyl)-1,1-dimethylethylamino]-3-(o-chloro-p-hydroxyphenoxy)-propanol-2; and
1-[2-phenyl-1,1-dimethylethylamino]-3-p-hydroxphenoxy propanol-2.

Salt forming acids may be used in preparing therapeutically acceptable salts of the compounds. These are: hydrohalogen acids, sulphuric acids, phosphoric acid, nitric acid, perchloric acid, aliphatic, alicyclic, aromatic or heterocyclic carboxy or sulphonic acids, such as formic, acetic, propionic, succinic, glycolic, lactic, malic, tartaric, citric, ascorbic, maleic, hydroxymaleic, or pyruvic acid, phenylacetic, benzoic, p-aminobenzoic, anthranilic, p-hydroxybenzoic, salicyclic or p-aminosalicyclic acid, embonic acid, methanesulphonic, ethanesulfonic, hydroxyethane sulfonic, ethylenesulfonic, halogen-benzenesulfonic, toluenesulfonic, naphthylsulfonic or sulfanilic acid, methionine, tryptophane, lysine or arginine.

The substances are intended to be administered orally or parenterally for acute and chronic treatment of cardiac failure, specifically, ventricular myocardial failure (disease conditions with a diminution in ventricular contractibility below that of a normal heart such that the capacity of the myocardium, at any given fiber length, to develop tension or to shorten against a load is so impaired as to compromise the circulation). Accordingly, the substances are intended to mitigate symptoms and signs of cardiac failure such as dyspnea, cyanosis, pulmonary edema, increased venous pressure, liver enlargement, and peripheral edema.

The substances may be used alone and in combination with other therapeutic measures, such as administration of digitalis and diuretic drugs. Also, the substances may be used in combination with other measures in treating cardiogenic shock, the condition associated with reduced arterial blood pressure which often complicates myocardial infarction. Another use for the substances is in treatment of bradycardia, that is, conditions with slow heart rhythm where the weak positive chronotropic effect in combination with the positive inotropic effect of the substances can be expected to be of therapeutic value.

The biological effects of the new compounds have been tested, and the different tests carried out will be shown and explained below. Based on these tests, and other tests, it is believed that the effect of the novel compounds of the present invention depends on the activation of the adrenergic receptors which control the contractility of the heart.

EXAMPLE A

Beta-Adrenergic Effects of Isoprenaline and Compounds According to the Invention. On An Anesthetized Cat Pretreated With Reserpine Chronotropic (heart frequency) and vasodilating effects were measured using anesthetized cats with isoprenaline as a reference compound. This technique has been recognized in the literature as a valuable means for identifying β-receptor compounds; see β-receptor effects. "Pharmacological Studies of Two New Cardioselective Adrenergic β-receptor Blockers", B. Ablad et al., Life Sciences, Vol. 12, Part 1, pp. 107–119 (1973),* and "Influence of Metroprotol and Propranolol on Hemodynamic Effects Induced by Adrenalin and Physical Work", G. Johnson, to be published in Actan Pharmacol & Toxical Suppl. 3 (1975).*

*The authors of these publications are employed by A. B. Hassle, the assignee of this application; one of the co-authors of B. Ablad et al is Enar I. Carlsson, a co-applicant herein.

Cats having an average weight of 3 kg were treated with reserpine (5 mg/kg bodyweight intramuscularly) about 16 hours before the test. This treatment eliminated completely the reflex symphathetic control of the heart and the vascular tonus. When the cats had been anesthetized with Mebumal ® 30 mg/kg bodyweight i.p., artificial air respiration was started. The two vagus nerves were cut and the blood passing through a femoral artery was fed via a catheter and a pump back to the distal part of the vessel. A pressure transducer was connected in parallel by which the perfusion pressure, at a constant flow rate, was registered. When a constant flow of perfusion is maintained, the perfusion pressure is directly proportional to the peripheral resistance of the vascular bed of the hind limb.

Blood circulation in the foot was interrupted with a ligature. Heart frequency was registered with a cardiotachometer triggered by the ECG. The substances were administered intravenously in increasing doses and the dose-response curves of the heart frequency and the vasodilation were constructed.

In Table 1 below, the $ED_{50}$ values are given, i.e., the estimated doses which give 50% of maximal effect. Further, the dose ratios ($ED_{50}$ for vasodilation/$ED_{50}$ for heart frequency) are calculated. A dose ratio >1 indicates a heart selective effect. The values given represent the mean values of four experiments.

TABLE 1

| Compound (acc. to Ex.) | Affinity $ED_{50}$ ug/kg | | Selectivity $ED_{50}$ vasodilation $ED_{50}$ Heart frequency | Heart Frequency Response, Intrinsic Activity (% of IPR Response) |
|---|---|---|---|---|
| | Heart frequency | Vasodilation | | |
| Isoprenaline (IPR) | 0.05 | 0.01 | 0.2 | 100 |
| 1 | 30 | >1000 | >33 | 100 |
| 2 | 30 | >1000 | >33 | 86 |
| 3 | 62 | >1000 | >16 | 78 |
| 4 | 32 | >1000 | >31 | 86 |
| 5 | 11 | >1000 | >90 | 100 |
| 6 | 10 | >1000 | >100 | 97 |
| 7 | 32 | >1000 | >31 | 87 |
| 8 | 28 | >1000 | >35 | 87 |

The results show a striking specificity of action in increasing heart rate selectivity. While Compounds 1 through 8 are about 1/200 or less as potent as isoprenaline as regards the chronotropic effect, they were less than 1/100,000 as potent as isoprenaline as regards the vasodilating effect. The heart frequency response for compounds of the invention tested was about 80% or more of a maximum isoprenaline response.

The new compounds are obtained according to methods known per se. Thus, a compound of formula II

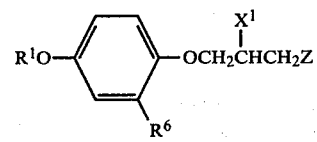

wherein $R^1$ and $R^6$ have the meanings given above, $X^1$ is a hydroxy group, Z is a reactive, esterified hydroxy group, or $X^1$ and Z together form an epoxy group is reacted with an amine of the formula $NH_2$-R, wherein R has the same meaning as given above.

A reactive, esterified hydroxy group is preferably a hydroxy group esterified with a strong, inorganic or organic acid, preferably a hydrohalogen acid, as hydrochloric acid, hydrobromic acid, or hydroiodic acid. Sulphuric acid or a strong organic sulphonic acid as a strong aromatic sulfonic acid, e.g., benzenesulfonic acid, 4-bromobenzenesulfonic acid or 4-toluenesulfonic acids may also be used. Thus, Z is preferably chloro, bromo or iodo.

This reaction is carried out in a common way. Using a reactive ester as a starting material, the preparation takes place preferably in the presence of a basic condensing agent and/or with an excess of an amine. Suitable basic condensing agents are, e.g., alkali metal hydroxides as sodium or potassium hydroxide, alkali metal carbonates as potassium carbonate and alkali metal alcoholates as sodium methylate, potassium ethylate and potassium tert.-butylate.

In the alternative, a compound of Formula III

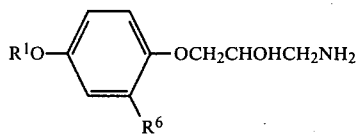

wherein $R^1$ and $R^6$ have the meanings given above is reacted with a compound of the formula Z-R, wherein R and Z have the same meanings as given above except for the case when $R^3$ is methyl.

This reaction is carried out in a common way, preferably in the presence of a basic condensing agent and/or an excess of an amine. Suitable basic condensing agents are, e.g., alkaline alcoholates, preferably sodium or potassium alcoholate, or also alkaline carbonates as sodium or potassium carbonate.

In still another procedure, a compound of Formula IV

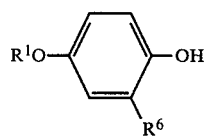

wherein $R^1$ and $R^6$ have the same meanings as given above is reacted with a compound of Formula V

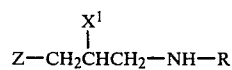

wherein Z, $X^1$ and R have the same meanings as given above.

This reaction is carried out in a common way. In those cases where reactive esters are used as starting material, the compound of Formula IV may suitably be used in the form of a phenolate as an alkali metal phenolate, preferably sodium phenolate. Alternatively, an acid binding agent, preferably a condensing agent, is used which will form a salt of the compound of Formula IV as an alkali metal alcoholate.

In another technique, a compound of Formula IV

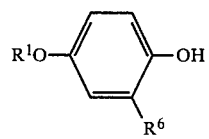

wherein $R^1$ and $R^6$ have the same meanings as given above, is reacted with a compound of Formula VI

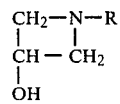

wherein R has the same meanings as given above.

This reaction is carried out in a common way. Thus, the reaction is carried out under alkaline conditions in a suitable solvent, as benzyl alcohol by boiling the reaction mixture for some hours. The phenol is primarily converted to its metal phenolate, as alkali metal phenolate, before it is added to the acetidinol of Formula VI.

Other techniques of preparation will be obvious to the ordinary chemist, depending upon the precursor material which is accessible from a synthetic standpoint. Potential percursor materials which, under appropriate circumstances may be relatively more accessible, include compounds such as Formula VII

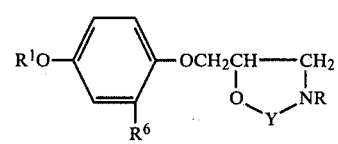

wherein Y is carbonyl or thiocarbonyl. and Shiff bases such as Formula VIII or Formula IX

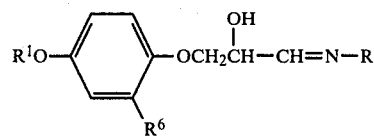

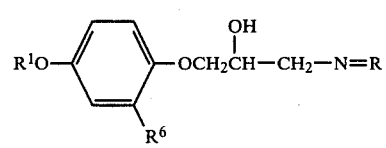

or cyclic tautomers thereof such as Formula X

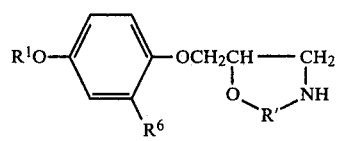

wherein $R^1H$ is R

Other potential percursors are compounds such as Formula XI and Formula XII

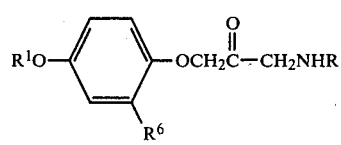

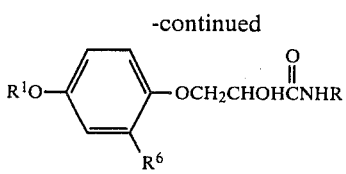

$$R^1O-\underset{R^6}{\underset{|}{\text{C}_6\text{H}_3}}-OCH_2CHOHCNHR \quad \text{XII}$$

Such precursors may be converted to a final product within the scope of the present invention by known techniques such as hydrolysis or hydrogeneration, care being taken in an appropriate case that the conversion step does not adversely affect the precursor material or the desired end product.

Depending on the process conditions and the starting material, the end product is obtained either in free form or in the form of its acid addition salt, which is included in the scope of the invention. Thus, for example, basic, neutral or mixed salts may be obtained as well as hemiamino, sesqui- or polyhydrates. Either may be used; and depending on the convenience of the ultimate end use the free base (if that is the initial reaction product) may be converted into the addition salt, or conversely.

In the preparation of acid addition salts preferably such acids are used which form suitable therapeutically acceptable salts. Such acids are, e.g., hydrohalogen acids, sulfuric acid, phosphoric acid, nitric acid, perchloric acid, aliphatic, alicyclic, aromatic or hetercyclic carboxy or sulfonic acids, as formic, acetic, propionic, succinic, glycolic, lactic, malic, tartaric, citric, ascorbic, maleic, hydroxymaleic or pyruvic acid, phenylacetic, benzoic, p-aminobenzoic, antranilic, p-hydroxybenzoic, salicylic or p-aminosalicylic acid, embonic acid, methanesulfonic, ethanesulfonic, hydroxyethanesulfonic, ethylenesulfonic acids, halogenbenzenesulfonic, toluenesulfonic, naphthylsulphonic acids, or sulfanilic acid, methionine, tryptophane, lysine or arginine.

These or other salts of the new compounds as, e.g., picrates, may also serve as purifying agents of the free bases obtained as the free bases are transformed into salts, these are separated and the bases, if desired, are then freed from the salts again.

The new compounds may, depending on the choice of starting materials and process, be present as optical antipodes or racemate, or, if they contain at least two asymmetric carbon atoms, be present as an isomer mixture (racemate mixture).

The isomer mixtures (racemate mixtures) obtained may, depending on physical-chemical differences of the components, be separated into the both stereoisomeric (diastereomeric) pure reacemate, e.g., by means of chromatography and/or fractionated crystallization.

The racemate obtained can be separated according to known methods, e.g., by means of recrystallization from an optically active solvent, by means of microorganisms, or by a reaction with optically active acids forming salts of the compound and separating the salts thus obtained, e.g., by means of their different solubility in the diasteremeres, from which the antipodes by the influence of a suitable agent may be set free. Suitably optically active acids are, e.g., the L- and D-forms of tartaric acid, di-o-tolyltartaric acid, malic acid, mandelic acid, camphorsulfonic acid or china acid. Preferably the more active part of the two antipodes is isolated.

In clinical use the compounds of the invention are administered normally orally, rectally or by injection in the form of a pharmaceutical preparation, which contains an active component either as free base or as pharmaceutically acceptable, non-toxic acid addition salt (as, e.g., the hydrochloride, lactate, acetate, sulphamate or the like) in combination with a pharmaceutically acceptable carrier. It should be understood in this respect that where reference is made to various novel compounds of the invention either the free amine base or the acid addition salts of the free base may be used as may be appropriate to a specific application.

It should also be understood that while, for the most part, pharmaceutical compositions within the scope of the present invention will be based on the preparation of a substantially pure compound within the scope of the generic formula I above, that the invention is not limited to the use of such isolated compounds. As a matter of manufacturing convenience, or for other reasons, it may be desirable to use a mixture of two or more compounds within the generic formula I, and such mixtures are contemplated as a part of the present invention.

The carrier may be a solid, semisolid or liquid diluent or a capsule. Usually the amount of active compound is between 0.1 to 95% by weight of the preparation, suitably between 0.5 to 20% by weight in preparations for injection and between 2 to 50% by weight in preparations for oral administration.

In the preparation of pharmaceutical preparations containing a compound of the present invention in the form of dosage units for oral administration the compound may be mixed with a solid, pulverulent carrier, as, e.g., with lactose, saccharose, sorbitol, mannitol, starch, as potato starch, corn starch amylopectin, cellulose derivatives or gelatine, as well as with an antifriction agent as magnesium stearate, calcium stearate, polyethyleneglycol waxes or the like, and be pressed into tablets. If coated tablets are wanted, the above prepared core may be coated with concentrated solution of sugar, which may contain, in addition, substances such as gum arabicum, gelatin, talc, titanium dioxide or the like. The tablets may be coated with a laquer dissolved in a volatile organic solvent or mixture of solvents. A dye may be added to this coating in order to easily distinguish between tablets with different active compounds or with different amounts of the active compound present.

In the preparation of soft gelatine capsules (pearl-shaped, closed capsules), which consist of gelatin and, e.g., glycerine or in the preparation of similar closed capsules the active compound is mixed with a vegetable oil. Hard gelatine capsules may contain granules of the active compound in combination with a solid, pulverulent carrier as lactose, saccharose, sorbitol, mannitol, starch (as, e.g., potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be present in the form of syrups or suspensions, e.g., solutions containing from about 0.2% by weight of about 20% by weight of the active substance described, whereby the residue consists of sugar and a mixture of ethanol, water, glycerol and propylene glycol. If desired, such liquid preparations may contain coloring agents, flavoring agents saccharine and carboxymethylcellulose as a thickening agent.

Solutions for parenteral administration by injection may be prepared as an aqueous solution of a watersoluble pharmaceutically acceptable salt of the active compound, preferably in a concentration from about 0.5% by weight to about 0.10% by weight. These solutions may also contain stabilizing agent and/or buffering agents and may suitably be available in different dosage unit ampoules.

By way of illustration, tablets for use may be prepared in accordance with the following method:

A binding agent is ground or sieved to a desired particle size convenient to processing. The binding agent is then homogenized and suspended in a solvent. The therapeutic compound and necessary suitable auxiliary agents are mixed during a continuous and constant mixing of the binding agent solution, and are moistened so that the mixture becomes uniform without overmoistening any parts. The amount of solvent is usually so adapted that the mass has the consistency of wet snow. The moistening of the pulverulent mixture with the binding agent solution causes the particles to gather together slightly to aggregates. The mass is then pressed through a stainless steel sieve having a mesh size of about 1 mm., and placed in thin layers on a tray to be dried. This drying has to be standardized carefully as the dampness of the granulate is of utmost importance for the following process. Drying in a fluid bed may possibly be used.

After the drying step the granules are sieved so that the particle size wanted is obtained.

Disintegrating, antifriction agents and antiadhesive agents are added to the so-called final mixture. After this mixture the mass is ready for the tabletting step.

The cleaned tablet punching machine is provided with punches and dies, and adjusted for the weight of the tablets and the degree of compression. The weight of the tablets is obviously selected to provide the desired dose in each tablet, and is calculated starting from the amount of therapeutic agent in the granules. The degree of compression affects the size of the tablet, its strength and its ability of disintegrate in water. The choice of compression pressure (0.5 to 5 ton) requires a balancing especially of the relative needs as respects tablet strength and tablet dispersibility. Frequently, tablets, especially these which are rough or bitter, are coated with a coating. This means that these are coated with a layer of sugar or some other suitable coating.

The daily dose of the active substance varies and is depending on the type of administration. Based experience with isoprenaline as well as other data anticipates that as a general rule the preferred dosage is in the order of 50 to 100 mg/day of active substance via peroral administration and 5 to 20 mg/day via intravenous administration in man.

The following illustrates the principle and the adaptation of invention, however, without being limited thereto. Temperature is given in degree Celsius.

EXAMPLE 1

Preparation of 1-[2-phenyl-2-hydroxy-1-methylethylamino]-3-p-hydroxyphenoxy propanol-2

2.5 g of 1,2-epoxy-3-p-benzyloxyphenoxy propane were mixed with 1.5 g of 1-phenyl-2-amino-propanol-1 and 25 ml of isopropanol and the total solution was refluxed for 1.5 hours. The solution was thereupon evaporated in vacuo; the residue was dissolved in 95% ethanol and treated with active carbon. The ethanol solution was filtered and hydrogenated using a Pd/C catalyst (10% Pd on carbon) and hydrogen at atmospheric pressure. The solution, thus hydrogenated to split off the benzyl group, was filtered and evaporated to dryness in vacuo. The base thus obtained was dissolved in acetone and the hydrochloride was precipitated using HCl in ether. The hydrochloride was filtered off and washed with acetonitrile. The yield of 1-[2-phenyl-2-hydroxy-1-methylethyl-amino]-3-p-hydroxyphenoxy propanol-2 was 1.4 g. Melting point 163° C. The structure was determined using NMR.

EXAMPLE 2

Ethyl-3-[3-p-hydroxyphenoxy-2-hydroxy)-propylamino]-butyrate was prepared according to Example 1 using 1,2-epoxy-3-p-benzyloxy-phenoxy-propane and 3-amino-butyric acid ethyl ester as starting materials. The base was obtained as a water soluble oil and its structure was determined by NMR and equivalent weight.

EXAMPLE 3

3-[3-p-hydroxyphenoxy-2-hydroxy-propylamino]-butyramide was prepared according to Example 1 using 1,2-epoxy-3-p-benzyloxyphenoxy-propane and 3-amino-butyramide as starting materials. The base was obtained as a water soluble oil and its structure was determined by NMR and equivalent weight.

EXAMPLE 4

1-[Hydroxy tert.-butylamino]-3-p-hydroxyphenoxy propanol-2 was prepared according to Example 1 using 1,2-epoxy-3-p-benzyloxy-phenoxy propane and 2-amino-2-methyl propanol-1 as starting material. The p-hydroxybenzoate was prepared. Melting point 190° C.

EXAMPLE 5

1-[2-p-Hydroxyphenyl)-1-methylethylamino]-3-p-hydroxyphenoxy propanol-2 was prepared according to Example 1 using 1,2-epoxy-3-p-benzyloxyphenoxypropane and 2-p-hydroxyphenyl-1-methylethylamine as starting material. The melting point of the hydrochloride is 190° C.

EXAMPLE 6

1-[2-(p-Hydroxyphenyl)-1,1-dimethylethylamino]-3-p-hydroxy-phenoxy propanol-2 was prepared according to Example 1, using 1,2-epoxy-3-p-benzyloxy-phenoxypropane and 2-p-hydroxyphenyl-1,1-dimethylethyl amine as starting materials. The melting point of the hydrochloride is 219° C.

EXAMPLE 7

1-[2-(p-chlorophenyl)-1-methylethylamino]-3-p-hydroxyphenoxy-propanol-2 was prepared according to Example 1, using 1,2-epoxy-3-p-benzyloxyphenoxy-propane and 2-p-chlorophenyl-1-methylethylamine as starting materials. The melting point of the hydrochloride is 122° C.

EXAMPLE 8

1-Cyclopentylamino-3-p-hydroxyphenoxy propanol-2 was prepared according to Example 1, using 1,2-epoxy-3-p-benzyloxyphenoxy propane and cyclopentylamine as starting materials. The melting point of the hydrochloride is 165° C.

EXAMPLE 9

1-[2-(p-hydroxyphenyl)1,1-dimethylethylamino]-3-o-chloro-p-hydroxyphenoxylpropanol-2 was prepared according to Example 1, using 1,2-epoxy-3-o-chloro-p-benzyloxyphenoxypropane and 2-p-hydroxyphenyl-1,1-dimethylethylamine as starting materials.

EXAMPLE 10

1-(2-phenyl-1,1-dimethylethylamino)-3-p-hydroxyphenoxy propanol-2 was prepared in accordance with Example 1 above using 1,2-epoxy-3-p-benzyloxyphenoxypropane and 2-phenyl-1,1-dimethylethylamine as starting materials. The melting point is 160° C. as hydrochloride.

EXAMPLE 11

10 g of p-benzyloxyphenylglycidylether in 100 ml of ethanol were saturated with gaseous ammonia and the mixture was heated in an autoclave on a boiling waterbath for 4 hours. The solvent was evaporated and the residue was dissolved in ethylacetate and HCl-gase was introduced. The hydrochloride then precipitated and it was filtered off and dissolved in 50 ml of ethanol to which 2-phenyl-1,1-dimethylethylamine and 15 g of $K_2CO_3$ had been added. The mixture was heated in an autoclave at 130° C. for 10 hours whereupon the solvent was evaporated and the residue was mixed with 100 ml of 2 N HCl and 100 ml of ether. The aqueous phase was separated off and was made alkaline with 2 N NaOH and extracted with ethyl acetate. The solvent phase was dried over $K_2CO_3$, whereupon 1-(2-phenyl-1,1-dimethylethylamino)-3-(p-benzyloxyphenoxy) propanol-2 was obtained. The compound was dissolved in ethanol and hydrogenated using a Pd/C catalyst and hydrogen in accordance with Example 1 above. The base obtained was converted to its hydrochloride, 1-(2-phenyl-1,1-dimethylethylamino)-3-(4-hydroxyphenoxy) propanol-2-hydrochloride, melting point 160° C.

EXAMPLE 12

2.4 g of sodium were dissolved in 100 ml of ethanol, whereupon 18.0 g of p-benzyloxyphenol and 21.7 g of 1-(2-phenyl-1,1-dimethylethylamino)-3-chloropropanol-2 were added. The mixture was heated in an autoclave on a boiling waterbath for 15 hours. Thereupon it was filtered and the filtrate was evaporated to dryness. The residue was made acidic with 2 N HCl and extracted with ether, whereupon the aqueous phase was made alkaline with 2 N NaOH and extracted with ethylacetate. The ethylacetate was dried over $MgSO_4$ and 1-(2-phenyl-1,1-dimethylethylamino)-3-[p-benzyloxyphenoxy]-propanol-2 was obtained and was hydrogenated and isolated in accordance with Example 1 above. M.p. 160° C.

EXAMPLE 13

In accordance with Example 12 above N-benzyl-1-(2-phenyl-1,1,-dimethylethylamino)-3-benzyloxyphenoxy)-propanol-2 was prepared from p-benzyloxyphenol and N-benzyl-1-(1-methyl-2-cyanoethyl)amino-3-chloropropanol-2-p-hydroxybenzoate, 10 g of the compound thus obtained were dissolved in 100 ml of ethanol, 0.5 g of Pd/C (10%) catalyst were added and hydrogenation was carried out until estimated amount of $H_2$ had been absorbed. After filtration the mixture was evaporated to dryness and the residue 1-(2-phenyl-1,1-dimethylethylamino-3-(p-hydroxyphenoxy)-propanol-2 was obtained.

EXAMPLE 14

12 g of 1-amino-3-(p-benzyloxyphenoxy)-propanol-2 prepared in accordance with Example 11 above were dissolved in 100 ml of methanol containing 10 g of p-chlorobenzylmethylether. The solution was cooled on an icebath and 10 g of sodiumborhydride was added little by little. The temperature was allowed to rise to room temperature and after 1 hour 200 ml of $H_2O$ were added and the mixture was extracted with ethylacetate. The ethylacetate phase was dried over $K_2CO_3$ and the compound 1-(2-chlorophenyl-1-methylethylamino)-3-[p-benzyloxy-phenoxy]-propanol-2 was obtained, and then hydrogenated and isolated in accordance with Example 1. The melting point of the hydrochloride of 1-(2-p-chlorophenyl-1-methylethylamino)-3-p-hydroxyphenoxypropanol-2 was 122° C.

EXAMPLE 15

11.6 g of p-benzyloxyphenol, 8.0 g of 1-(2-phenyl-1,1-dimethylethyl)-3-acetidinol, 50 g of benzylalcohol and 0.5 g of KOH was heated to 140° C. for 6 hours while stirring. After cooling the mixture was extracted with 2 N HCl. The aqueous phase was made alkaline and the compound was extracted with chloroform. The chloroform phase was dried and evaporated. 1-(2-phenyl-1,1-dimethylethylamino)-3-(p-benzyloxyphenoxy)-propanol-2 was obtained and then hydrogenated and isolated as the p-hydroxy compound in accordance with Example 1.

EXAMPLE 16

A syrup containing 2% (weight per volume) of active substance was prepared from the following ingredients:

| | |
|---|---|
| 1-[2-phenyl-2-hydroxy-1-methylethylamino]-3-p-hydroxyphenoxy propanol-2 HCl | 2.0 g |
| Saccharine | 0.6 g |
| Sugar | 30.0 g |
| Glycerine | 5.0 g |
| Flavoring agent | 0.1 g |
| Ethanol 96% | 10.0 ml |
| Distilled water | ad 100.0 ml |

Sugar, saccharine and the active compound were dissolved in 60 g of warm water. After cooling glycerine and e solution of flavoring agents dissolved in ethanol were added. To the mixture water was then added to 100 ml.

The above given active substance may be replaced with other pharmaceutically acceptable acid addition salts.

EXAMPLE 17

1-[2-p-hydroxyphenyl-1,1-dimethylethylamino-3-p-hydroxyphenoxyl-propanol-2 hydrochloride (250 g) was mixed with lactose (175.8 g) potato starch (169.7 g) and colloidal silicic acid (32 g). The mixture was moistened with a 10% solution of gelatine and was granulated through a 12-mesh sieve. After drying potato starch (160 g), talc (50 g) and magnesium stearate (5 g) were admixed and the mixture thus obtained was pressed into tablets (10,000) which contained 25 mg of substance. The tablets provided with a breaking score to give fractional doses of the basic 25 mg dosage unit thereof when broken.

EXAMPLE 18

Granules were prepared from 1-(hydroxytert-.butylamino)-3-p-hydroxyphenoxy-propanol-2-p-hydroxybenzoate (250 g), lactose (175,9 g) and an alcoholic solution of polyvinylpyrrolidone (25 g). After the drying step the granules were mixed with talc (25 g) potato starch (40 g) and magnesium stearate (2.50 g) and was pressed into 10,000 tablets. These tablets were coated with a 10% alcoholic solution of shellac and thereupon with an aqueous solution containing saccharose (45%), gum arabicum (5%), gelatine (4%) and dyestuff (0.2%). Talc and powder sugar were used for powdering after the first five coatings. The coating was then coated with a 66% sugar syrup and polished with a 10% carnauba wax solution in carbon tetrachloride.

EXAMPLE 19

1-Cyclopentylamino-3-p-hydroxyphenoxy-propanol-2-hydrochloride (1 g), sodium chloride (0.8 g) and ascorbic acid (0.1 g) were dissolved in sufficient amount of distilled water to give 100 ml of solution. This solution, which contains 10 mg of active substance of each ml, was used in filling ampoules, which were sterilized by heating at 120° C. for 20 minutes.

We claim:

1. A compound of formula I(a)

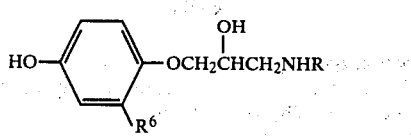

wherein
R is

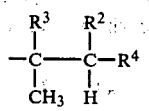

wherein
$R^2$ is hydrogen;
$R^3$ is selected from the group consisting of hydrogen and methyl;
$R^4$ is selected from the group consisting of

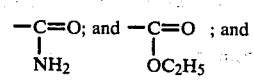

$R^6$ is selected from the group consisting of hydrogen, halogen and allyl; or
a pharmaceutically acceptable salt of a compound according to formula I(a).

2. The compound, according to claim 1, ethyl-3-[3-p-hydroxyphenoxy]-2-hydroxypropylamino butyrate.

3. The compound, according to claim 1, 3-[3-p-hydroxyphenoxy-2-hydroxy-propylamino]-butyramide.

4. A method of stimulating the β-receptors of the heart by administering to mammals, including man, suffering from symptoms and signs of cardiac failure, in an amount sufficient to mitigate said symptoms, a compound of the general formula I(a)

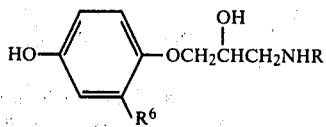

wherein
R is

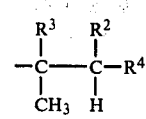

wherein
$R^2$ is hydrogen;
$R^3$ is selected from the group consisting of hydrogen and methyl;
$R^4$ is selected from the group consisting of

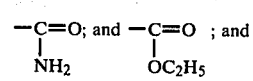

$R^6$ is selected from the group consisting of hydrogen, halogen and allyl;
or a pharmaceutically acceptable salt of a compound according to formula I(a).

5. A method according to claim 4 wherein said compound is ethyl 3-[3-p-hydroxyphenoxy]-2-hydroxypropylamino butyrate.

6. A method according to claim 4 wherein said compound is 3-[3-p-hydroxyphenoxy-2-hydroxypropylamino]butyramide.

7. A pharmaceutical preparation in dosage unit form for the treatment of mammals, including man, suffering from symptoms of cardiac failure, containing as an active ingredient an amount effective to mitigate said symptoms of at least one compound of the formula I(a)

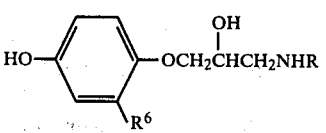

wherein
R is

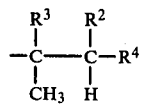

wherein
$R^2$ is hydrogen;
$R^3$ is selected from the group consisting of hydrogen and methyl;
$R^4$ is selected from the group consisting of

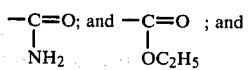

$R^6$ is selected from the group consisting of hydrogen, halogen and allyl;
or a pharmaceutically acceptable salt of a compound according to formula I(a).

8. A pharmaceutical preparation according to claim 7, wherein said compound is ethyl 3-[3-p-hydroxyphenoxy]-2-hydroxypropylamino butyrate.

9. A pharmaceutical preparation according to claim 7, wherein said compound is 3-[3-p-hydroxyphenoxy-2-hydroxypropylamino]-butyramide.

10. A compound of formula I(b)

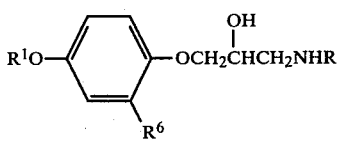

wherein
$R^1$ is selected from the group consisting of benzyl, tosyl, mesyl and

$R^5$ being hydrogen, straight or branched aliphatic alkyl having 1 to 7 carbon atoms, phenyl, benzyl, and phenylethyl, wherein the phenyl nucleus may be further substituted with alkyl having 1 to 4 carbon atoms, alkoxy having 1 to 4 carbon atoms, alkoxyalkyl having 2 to 8 carbon atoms or halogen, in any position;
R is selected from the group consisting of cycloalkyl having at most 6 carbon atoms, and

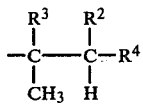

wherein
$R^2$ is selected from the group consisting of hydrogen and hydroxy;
$R^3$ is selected from the group consisting of hydrogen and methyl;
$R^4$ is selected from the group consisting of

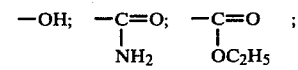

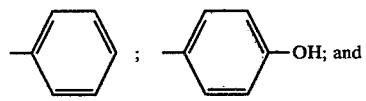

when $R^2$ is hydrogen, and $R^4$ is selected from the group consisting of

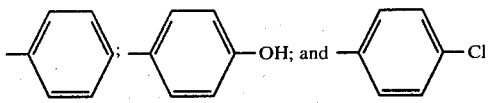

wherein $R^2$ is OH; and
$R^6$ is selected from the group consisting of hydrogen, halogen and allyl;
or a pharmaceutically acceptable salt of a compound according to formula I(b).

11. A method of stimulating the β-receptors of the heart by administering to mammals, including man, suffering from symptoms and signs of cardiac failure, in an amount sufficient to mitigate said symptoms, a compound of the general formula I(b)

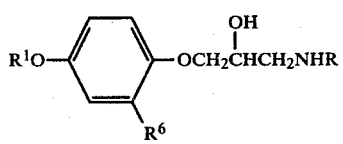

wherein
$R^1$ is selected from the group consisting of benzyl, tosyl, mesyl and

$R^5$ being hydrogen, straight or branched aliphatic alkyl having 1 to 7 carbon atoms, phenyl, benzyl, and phenylethyl, wherein the phenyl nucleus may be further substituted with alkyl having 1 to 4 carbon atoms, alkoxy having 1 to 4 carbon atoms, alkoxyalkyl having 2 to 8 carbon atoms or halogen, in any position;
R is selected from the group consisting of cycloalkyl having at most 6 carbon atoms, and

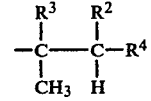

wherein
$R^2$ is selected from the group consisting of hydrogen and hydroxy;
$R^3$ is selected from the group consisting of hydrogen and methyl;
$R^4$ is selected from the group consisting of

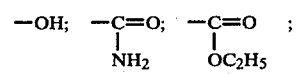

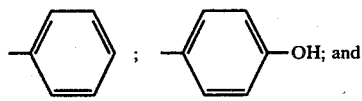

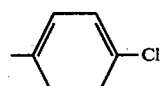

when R² is hydrogen, and R⁴ is selected from the group consisting of

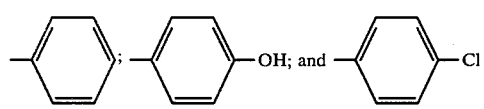

wherein R² is OH; and
R⁶ is selected from the group consisting of hydrogen, halogen and allyl;
or a pharmaceutically acceptable salt of a compound according to formula I(b).

12. A pharmaceutical preparation in dosage unit form for the treatment of mammals, including man, suffering from symptoms of cardiac failure, containing as an active ingredient an amount effective to mitigate said symptoms of at least one compound of the formula I(b)

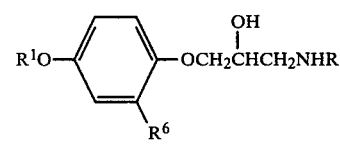

wherein
R¹ is selected from the group consisting of benzyl, tosyl, mesyl and

R⁵ being hydrogen, straight or branched aliphatic alkyl having 1 to 7 carbon atoms, phenyl, benzyl, and phenylethyl, wherein the phenyl nucleus may be further substituted with alkyl having 1 to 4 carbon atoms, alkoxy having 1 to 4 carbon atoms, alkoxyalkyl having 2 to 8 carbon atoms or halogen, in any position;

R is selected from the group consisting of cycloalkyl having at most 6 carbon atoms, and

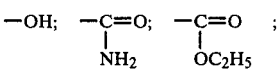

wherein
R² is selected from the group consisting of hydrogen and hydroxy;
R³ is selected from the group consisting of hydrogen and methyl;
R⁴ is selected from the group consisting of

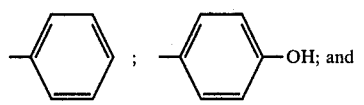

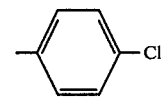

when R² is hydrogen, and R⁴ is selected from the group consisting of

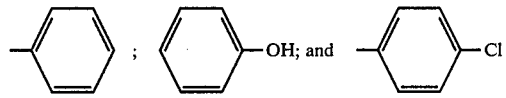

wherein R² is OH; and
R⁶ is selected from the group consisting of hydrogen, halogen and allyl;
or a pharmaceutically acceptable salt of a compound according to formula I(b).

* * * * *

UNITED STATES PATENT AND TRADEMARK OFFICE
CERTIFICATE OF CORRECTION

PATENT NO. : 4,336,267
DATED : June 22, 1982
INVENTOR(S) : Carlsson et al.

It is certified that error appears in the above—identified patent and that said Letters Patent is hereby corrected as shown below:

Col. 3, line 58, "A. B." should read --AB--.

Col. 9, line 49, "administation" should read --administration--.

Col. 12, line 14, "(2-chlorophenyl" should read --(2-p-chloro-phenyl--;

line 20, insert a hyphen after "yphenoxy".

Col. 14, line 36, insert a hyphen before "butyramide".

Signed and Sealed this

Twenth-eighth Day of September 1982

[SEAL]

Attest:

GERALD J. MOSSINGHOFF

Attesting Officer

Commissioner of Patents and Trademarks